US008450514B2

(12) United States Patent
Schubert et al.

(10) Patent No.: US 8,450,514 B2
(45) Date of Patent: May 28, 2013

(54) POLYETHER ALCOHOLS BEARING ALKOXYSILYL GROUPS BY ALKOXYLATION OF EPOXY-FUNCTIONAL ALKOXYSILANCES OVER DOUBLE METAL CYANIDE (DMC) CATALYSTS, AND PROCESSES FOR PREPARATION THEREOF

(75) Inventors: Frank Schubert, Neukirchen-Vluyn (DE); Wilfried Knott, Essen (DE)

(73) Assignee: Evonik Goldschmidt GmbH, Essen (DE)

( * ) Notice: Subject to any disclaimer, the term of this patent is extended or adjusted under 35 U.S.C. 154(b) by 934 days.

(21) Appl. No.: 12/389,667

(22) Filed: Feb. 20, 2009

(65) Prior Publication Data
US 2010/0041910 A1 Feb. 18, 2010

(30) Foreign Application Priority Data
Feb. 21, 2008 (DE) .......................... 10 2008 000 360

(51) Int. Cl.
*C08G 65/26* (2006.01)
(52) U.S. Cl.
USPC .......................................... 556/445; 556/446
(58) Field of Classification Search
None
See application file for complete search history.

(56) References Cited

U.S. PATENT DOCUMENTS
3,446,757 A 5/1969 Vandenberg
2009/0118411 A1 5/2009 Kimura et al.

FOREIGN PATENT DOCUMENTS
| EP | 1 586 597 | 10/2005 |
| WO | WO 01/21718 | 3/2001 |
| WO | WO 2005/078036 | 8/2005 |
| WO | WO 2008/004482 | 1/2008 |

OTHER PUBLICATIONS
Machine translation of WO2005/078036 (2005).*
Hsien-Ming, Kao; Macromolecules, 2007, 40, pp. 8673-8683, American Chemical Society, 2007.

* cited by examiner

*Primary Examiner* — Yevegeny Valenrod
(74) *Attorney, Agent, or Firm* — Frommer Lawrence & Haug LLP

(57) ABSTRACT

Polyether alcohols having alkoxysilyl groups, the use thereof and a process for their preparation by means of DMC catalysis, characterized in that one or more epoxy-functional alkoxysilanes are added individually or in a mixture with further epoxide compounds and optionally further comonomers, either in block form or in random distribution, onto a chain starter of the formula (VII) $R^1$—H(VII) having at least one reactive hydroxyl group, where $R^1$ is a saturated or unsaturated, optionally branched radical, or a polyether radical of the alkoxy-, arylalkoxy or alkylarylalkoxy group type, in which the carbon chain may be interrupted by oxygen atoms or corresponds to a polyetheralkoxy radical or to a singularly or multiply fused phenolic group.

12 Claims, 1 Drawing Sheet

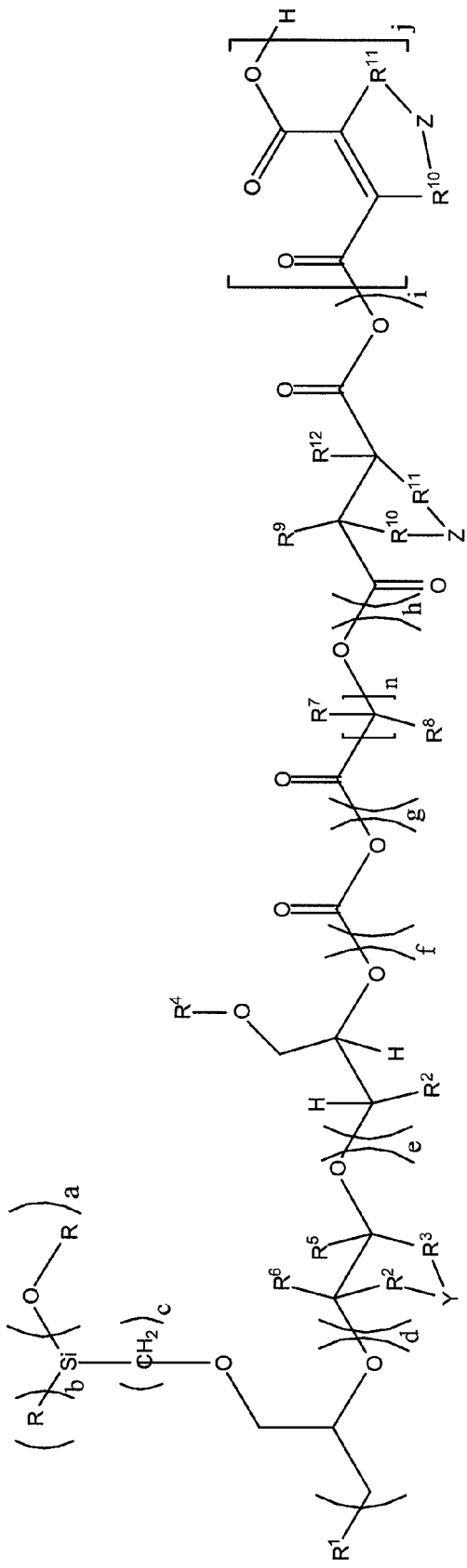
Formula (VIII)

POLYETHER ALCOHOLS BEARING ALKOXYSILYL GROUPS BY ALKOXYLATION OF EPOXY-FUNCTIONAL ALKOXYSILANCES OVER DOUBLE METAL CYANIDE (DMC) CATALYSTS, AND PROCESSES FOR PREPARATION THEREOF

This application claims benefit under 35 U.S.C. 119(a) of German patent application DE 10 2008 000 360.3, filed on 21 Feb. 2008.

Any foregoing applications, including German patent application DE 102008000360.3, and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

The invention relates to novel polyether alcohols bearing alkoxysilyl groups by alkoxylation of epoxy-functional alkoxysilanes over double metal cyanide (DMC) catalysts, and processes for production thereof.

Conventional polyether alcohols, often also referred to simply as polyethers for short and formed predominantly from propylene oxide and ethylene oxide, have been known for some time and are prepared industrially in large amounts. They are used, inter alia, by reaction of polyisocyanates, as starting compounds for preparing polyurethanes or else for preparing surfactants.

Most processes for preparing alkoxylation products (polyethers) make use of basic catalysts, for example of the alkali metal hydroxides and of the alkali metal methoxides.

Particularly widespread and known for many years is the use of KOH. Typically, a usually low molecular weight hydroxy-functional starter such as butanol, allyl alcohol, propylene glycol or glycerol is reacted in the presence of the alkaline catalyst with an alkylene oxide such as ethylene oxide, propylene oxide, butylene oxide or a mixture of different alkylene oxides to give a polyoxyalkylene polyether. The strongly alkaline reaction conditions in this so-called living polymerization promote various side reactions. Rearrangement of propylene oxide to allyl alcohol, which itself functions as a chain starter, and chain termination reactions result in formation of polyethers with a relatively wide molar mass distribution and unsaturated by-products. Especially with allyl alcohol as the starter alcohol, the alkoxylation reaction performed under alkaline catalysis also gives rise to propenyl polyethers. These propenyl polyethers are found to be unreactive by-products in the hydrosilylating further processing to give SiC-supported silicone polyether copolymers, and are additionally—as a result of the hydrolytic lability of the vinyl ether bond present therein and release of propionaldehyde—an undesired source of olfactory product nuisance. This is described, for example, in EP-A-1431331 (US 2004132951).

One of the disadvantages of base-catalysed alkoxylation is undoubtedly the necessity to free the resulting reaction products from the active base with the aid of a neutralization step. It is then absolutely necessary to distillatively remove the water formed in the neutralization and to remove the salt formed by filtration.

As well as the base-catalysed reaction, acid catalyses for alkoxylation are also known. For instance, DE 10 2004 007561 describes the use of $HBF_4$ and of Lewis acids, for example $BF_3$, $AlCl_3$ and $SnCl_4$, in alkoxylation technology.

A disadvantage in the acid-catalysed polyether synthesis is found to be the inadequate regioselectivity in the ring-opening of unsymmetrical oxiranes, for example propylene oxide, which leads to polyoxyalkylene chains with some secondary and some primary OH termini in a manner which cannot be controlled in an obvious way. As in the case of the base-catalysed alkoxylation reaction, a workup sequence of neutralization, distillation and filtration is indispensable here too. When ethylene oxide is introduced as a monomer into the acid-catalysed polyether synthesis, the formation of dioxane as an undesired by-product is to be expected.

Acid- and/or base-labile systems cannot, however, be alkoxylated successfully in any way under the conditions detailed. This is particularly true of organosilica derivatives such as alkoxysilane derivatives, which exhibit a marked tendency to acid- or base-induced condensation and crosslinking reaction. This is the more significant in that both the acid- and the base-induced alkoxylation reaction typically require a downstream workup in aqueous medium (neutralization, salt removal, distillation to remove the water).

Organic alkoxysilane compounds, such as 3-glycidyloxypropyltrimethoxysilane or 3-glycidyloxypropyl-triethoxysilane, which are obtainable, for example, under the respective trade names DYNASYLAN® GLYMO and DYNASYLAN® GLYEO (trademarks of Evonik Degussa GmbH), are used in the preparation of organically modified networks in the sol-gel process, which serves as a key process for production of nanocomposites, which afford coating systems with improved properties with regard to hardness, scratch resistance and abrasive resistance, thermal resistance, and solvent and acid stability. Alkoxysilane compounds additionally find various uses in sealants and adhesives, and generally as reactive adhesion promoters and primers for various substrates, such as metals, glass and glass fibres/glass fabrics for fibre-reinforced composite materials, and for surface treatment of, for example, pigments and fillers in coatings.

There has no been lack of efforts to improve the profiles of properties of alkoxysilane compounds by chemical modifications in order to open up still further fields of use for this important product class. For instance, the literature discloses combining the profile of properties of alkoxylation products (polyethers) with those of crosslinkable compounds bearing especially alkoxysilyl groups. For instance, DE 69831518 T2 applies, inter alia, to the modification of polyether alcohols with alkoxysilanes bearing, for example, isocyanate groups with urethanizing linkage. In addition, for the alkoxysilyl modification, the hydrosilylating attachment of alkoxymono-hydridosilanes to polyetherols which have been modified beforehand with olefinically unsaturated end groups is also selected.

JP 11021463 relates to a process for preparing trialkoxysilyl-terminated polyoxyalkylene ethers which derive from glycerol as the trifunctional alcohol, by modifying the particular glycerol polyether triols with trialkoxysilanes bearing isocyanate groups with urethanizing linkage.

Patent JP 08295805 claims an essentially comparable process which comprises the trialkoxysilyl modification of dipropylene glycol polyether diols prepared via DMC catalysis with trialkoxysilanes bearing isocyanate groups.

Documents JP 09012863, JP 09012861 and JP 07062222 claim a process for preparing polyetherols modified exclusively terminally with hydrolysable tialkoxysilyl functions, for example glycerol polyetherols, which are first prepared via DMC catalysis, then converted to the corresponding allyl ethers by adding alkali metal alkoxide and allyl chloride, and then converted by platinum metal-catalysed hydrosilylation to the alkoxysilyl-terminated target products.

All processes described in the prior art are thus suitable only for preparing polyoxyalkylene compounds modified exclusively terminally with trialkoxysilyl groups and in no way for simple and/or multiple modification of polyether chains with trialkoxy functions, even within the sequence of oxyalkylene units.

It is therefore an object of the present invention to overcome the outlined deficiencies of the prior art and to provide both novel polyether structures with alkoxysilane functions within the sequence of oxyalkylene units of the polyether chain and novel multialkoxysilyl-terminated polyether structures, and also a novel alkoxylation reaction for preparing these polyethers.

FIG. 1 illustrates a polyether structure according to an embodiment as set forth in the present disclosure.

In the context of this application, the inventive products are referred to as polyethers or polyetherols and/or derivatives thereof, even if the process affords substances with varying functionality as a result of the possible reactants. However, what is common to all products is that one terminal OH group is formed.

It has now been found that, surprisingly, alkoxysilanes bearing epoxy functions can be alkoxylated selectively in an advantageous and simple manner in the presence of known double metal cyanide catalysts, also known as DMC catalysts, without the tendency to undesired side reactions which is characteristic of this substance group (condensation and crosslinking reactions) being observed under the reaction conditions.

The process claimed in accordance with the invention for the first time opens up the possibility of undertaking, in a very simple and reproducible manner, the single and/or multiple alkoxysilyl group modification of polyoxyalkylene compounds not only terminally but also within the sequence of oxyalkylene units. Proceeding from a starter with reactive hydrogen, even the alkoxylating homopolymerization of alkoxysilanes bearing epoxy groups is possible.

The process claimed in accordance with the invention ensures the synthetic freedom to select between polyoxyalkylene groups having alkoxysilyl groups, which contain the alkoxysilyl functions which give rise to hydrolysing crosslinking in terminal form or in isolated form or in cumulative blocks or else scattered randomly in the polyoxyalkylene chain.

By using the processes according to the art only silylgroup-terminated prepolymers are accessible.

The compounds according to the invention show remarkable differences to oligomers or polymers prepared by classical processes. By the systematic and variable building of the polymer chain by insertion of functional groups which may have block or statistical distribution, also the silyl functionalisation is randomly or in form of blocks distributed over the chain; furthermore the silyl functionalisation may or may not be located at the chain termini.

An inseparably part of the inventive process for the alkoxylation of epoxyfuntional alkoxy silanes is the specific feature that the modified chain termini also shows a (secondary) OH-functionality, arising from the epoxide ring opening of the respective last epoxy monomer which has been added to the OH-functional end of the growing chain. An end capping of this terminal OH-group will not happen in difference to other known state of the art processes teaching the production of silyl terminated prepolymers.

Thus in the products prepared by direct alkoxylation every —O—$(CH_2)_c$—$Si(R)_b(OR)_a$-group is integrated into the prepolymer chain by an alpha spacing oxypropylen function.

The oxypropylen function is part of the ring opened epoxy functional alkoxysilane, which has been added by the DMC reaction.

As a matter of principle the products according to the inventive process are different from those prepolymers accessible form state of the art processes, which have the —O—$(CH_2)_c$—$Si(R)_b(OR)_a$-group directly bound to the polymer-radical without any spacer group.

By the inventive process non-classical, being not covered by state of the art, prepolymers can be produced. Even the cross linked, polymerized polymers derivable from those prepolymers are therefore also non-classical in their structure.

The simple insertion of a polymer fragment free of alkoxysilyl-groups within the chain and/or terminal functionalisation of a standard and therefore known in the art polymer radical will never yield in the prepolymer structures according to the invention.

Taking into account the structural differences of the inventive compounds/prepolymers, in the present application the term 'modified polymer' or 'modified polymer chain' will be used, whereas classical polymers, showing a block or randomly distribution of monomer units the term 'polymer' will only be used.

The alkoxysilyl compounds (I) containing epoxy groups used in the process according to the invention are compounds of the general type:

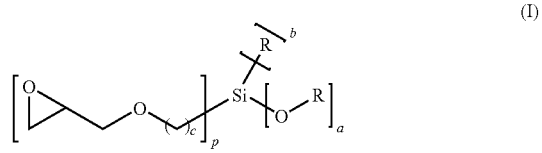

where
R represents one or more identical or different radicals selected from linear and branched, saturated, monounsaturated or polyunsaturated alkyl radicals having 1 to 20 and especially 1 to 6 carbon atoms, or haloalkyl groups having 1 to 20 carbon atoms. R preferably corresponds to methyl, ethyl, propyl, isopropyl, n-butyl and sec-butyl groups, and especially ethyl or methyl groups.
a represents an integer of 1 to 3, preferred 3
b an integer of 0 to 3, preferred 0 to 1 and most preferred 0 whereas the sum of a and b is 3,
c an integer of 0 to 24, preferably 0 to 12, more preferred 0 to 8 and even most preferred 0 to 4 and p is an integer which is the difference of 4-a-b.

The double metal cyanide catalysts (DMC catalysts) used for the process claimed in accordance with the invention have been known in terms of their preparation and use as alkoxylation catalysts since the 1960s and are described, for example, in U.S. Pat. Nos. 3,427,256, 3,427,334, 3,427,335, 3,278,457, ,278,458 or 3,278,459. Among the ever more effective types of DMC catalysts which have been developed further in the subsequent years and are described, for example, in U.S. Pat. Nos. 5,470,813 and 5,482,908 are specifically zinc hexacyanocobalt complexes. By virtue of their exceptionally high activity, only small catalyst concentrations are required to prepare polyetherols, and so the workup stage which is needed for conventional alkaline catalysts—consisting of neutralization, precipitation and the removal of the catalyst by filtration—at the end of the alkoxylation process can be dispensed with. The high selectivity of the DMC-catalysed alkoxylation is responsible for the fact that, for example, propylene oxide-based polyethers contain only very small proportions of unsaturated by-products.

The state of the art refers to various alkoxylation processes which make use of catalysis with double metal cyanide catalysts. As a reference, reference may be made here, for example, to EP-A-1017738 (U.S. Pat. No. 6,077,978), U.S. Pat. No. 5,777,177, EP-A-0981407 (U.S. Pat. No. 5,844,070), WO 2006/0028079 (US 2007225394) and EP-A 1474464 (U.S. Pat. No. 7,312,363).

It has been found that, surprisingly, not only conventional alkylene oxides, such as ethylene oxide, propylene oxide and 1,2-butylene oxide, but also the epoxy-functional alkoxysilanes which are known for their hydrolysis sensitivity, such as 3-glycidyloxypropyltrimethoxysilane or 3-glycidyl-oxypropyltriethoxysilane, can be alkoxylated in a simple manner in the presence of DMC catalysts. Such substituted silane compounds are polymerized under the conditions of the DMC catalysis quantitatively, selectively and sufficiently gently that the process according to the invention opens up the possibility of preparing a novel inventive product class of mono- and poly-alkoxysilyl-modified polyoxyalkylene compounds to obtain the hydrolysis-sensitive and crosslinkable alkoxysilyl groups.

There is thus provided a process for preparing polyether alcohols having crosslinkable alkoxysilyl groups by means of DMC catalysis, in which one or more epoxy-functional alkoxysilanes of the formula (I) are added individually or in a mixture with further epoxide compounds of the formulae (II) or (III) and optionally further comonomers such as lactones (IV), cyclic anhydrides (V), (VI), carbon dioxide or oxetanes, either in block form or randomly, onto a chain starter of the formula (VII) having at least one reactive hydrogen. The alkoxysilane monomers bearing at least one epoxy group may be scattered in the modified polymer chain as desired or else be arranged in the chain terminal position in the modified polymer structure.

It is a further aim of the process according to the invention to obtain the advantages known from the double metal cyanide systems of high reaction rate and of dispensing with the catalyst deactivation and removal.

It is a further aim of the process according to the invention to preserve the hydrolysis-sensitive alkoxysilyl groups under the reaction conditions of the selective DMC-catalysed alkoxylation and hence to provide access to a novel, likewise inventive class of crosslinkable polyethers or organically modified alkoxysilane compounds.

The silicon compounds used in accordance with the invention as epoxy-functional alkoxysilanes are compounds of the general formula (I)

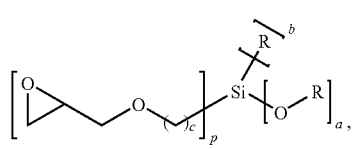

(I)

where
R represents one or more identical or different radicals selected from linear and branched, saturated, monounsaturated or polyunsaturated alkyl radicals having 1 to 20 and especially 1 to 6 carbon atoms, or haloalkyl groups having 1 to 20 carbon atoms. R preferably corresponds to methyl, ethyl, propyl, isopropyl, n-butyl and sec-butyl groups;
a represents an integer of 1 to 3, preferred 3
b an integer of 0 to 3, preferred 0 to 1 and most preferred 0 whereas the sum of a and b is 3,
c an integer of 0 to 24, preferably 0 to 12, more preferred 0 to 8 and even most preferred 0 to 4 and is especially equal to 1 or 3,
and p is an integer which is the difference of 4-a-b.

A nonexclusive list of such epoxy group-substituted alkoxysilanes of the formula (I), which can be used alone or in mixtures with one another or in combination with epoxide compounds of the formulae (II) and (III), comprises, for example, 3-glycidyloxypropyltri-methoxysilane, 3-glycidyloxypropyltriethoxysilane, 3-glycidyloxypropyltripropoxysilane, 3-glycidyloxypropyl-triisopropoxysilane, bis(3-glycidyloxypropyl)dimethoxy-silane, bis(3-glycidyloxypropyl)diethoxysilane, 3-glycidyloxyhexyltrimethoxysilane, 3-glycidyloxyhexyltriethoxysilane, 3-glycidyloxypropylmethyldimethoxy-silane, 3-glycidyloxypropylethyldiethoxysilane.

The epoxy-functional alkoxysilanes of the formula (I) can be used in the DMC-catalysed alkoxylation to prepare crosslinkable polyethers by the process according to the invention, as required, in any addition sequence successively or in a mixture with alkylene oxides of the general formula (II)

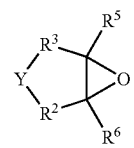

(II)

where $R^2$ and $R^3$, and $R^5$ and $R^6$, are the same or are each independently H or a saturated or optionally mono- or poly-unsaturated, optionally mono- or polyvalent hydrocarbon radical which also has further substitution, where the $R^5$ or $R^6$ radicals are a monovalent hydrocarbon radical. The hydrocarbon radical may be bridged cycloaliphatically via the fragment Y; Y may be absent, or else may be a methylene bridge having 1 or 2 methylene units, when Y is 0, $R^2$ or $R^3$ are each independently a linear or branched radical having 1 to 20 and preferably 1 to 10 carbon atoms, more preferably a methyl, ethyl, propyl or butyl radical, vinyl, allyl or phenyl radical. Preferably, at least one of the two $R^2$ and $R^3$ radicals in formula (II) is hydrogen. Particular preference is given to using, as the alkylene oxides, ethylene oxide, propylene oxide, 1,2- or 2,3-butylene oxide, isobutylene oxide, 1,2-dodecene oxide, styrene oxide, cyclohexene oxide (here, $R^2$-$R^3$ is a —$CH_2CH_2CH_2CH_2$— group, and Y is thus —$CH_2CH_2$—) or vinylcyclohexene oxide or mixtures thereof. The hydrocarbon radicals $R^2$ and $R^3$ of the formula (II) may in turn have further substitution and bear functional groups such as halogens, hydroxyl groups or glycidyl-oxypropyl groups. Such alkylene oxides include epichlorohydrin and 2,3-epoxy-1-propanol.

It is likewise possible to use glycidyl compounds such as glycidyl ethers and/or glycidyl esters of the general formula (III)

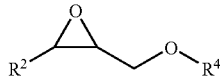

(III)

in which at least one glycidyloxypropyl group is bonded via an ether or ester function $R^4$ to a linear or branched alkyl radical of 1 to 24 carbon atoms, an aromatic or cycloaliphatic radical, in combination with the epoxy-functional alkoxysilanes described in formula (I) and optionally in addition to the alkylene oxides of the formula (II); $R^2$ does have the same definition as given under formula (II). This class of compounds includes, for example, allyl glycidyl ether, butyl glycidyl ether, 2-ethylhexyl glycidyl ether, cyclohexyl glycidyl ether, benzyl glycidyl ether, $C_{12}/C_{14}$-fatty alcohol glycidyl ether, phenyl glycidyl ether, p-tert-butylphenyl glycidyl ether or o-cresyl glycidyl ether. Glycidyl esters used with preference are, for example, glycidyl methacrylate, glycidyl acrylate or glycidyl neodecanoate. It is equally possible to use polyfunctional epoxide compounds, for example 1,2-ethyl diglycidyl ether, 1,4-butyl diglycidyl ether or 1,6-hexyl diglycidyl ether.

The epoxy group-bearing alkoxysilanes of the formula (I) useable in accordance with the invention may—optionally in combination with further epoxides of the formula (II) and (III)—be copolymerized under the conditions of the DMC-catalysed alkoxylation also in a mixture with lactones of the formula (IV)

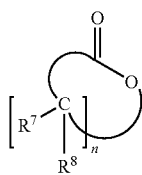

(IV)

where n is an integer of 2 to 8 and $R^7$ and $R^8$ are each independently hydrogen or alkyl, alkoxy, aryl or aralkyl groups with ring-opening polymerization to give crosslinkable alkoxysilane group-containing polyetheresters. Suitable lactones used in this connection may, for example, be ε-caprolactone, δ-valerolactone and γ-butyrolactone, and mixtures of different lactones. Preference is given to the use of ε-caprolactone as a comonomer. During the alkoxylation process, the particular epoxy and lactone monomers can be copolymerized in any sequence and in a variable amount successively or simultaneously in parallel to give polyetheresters with a blockwise or randomly distributed sequence of the individual monomer units.

Alternatively or additionally to lactones, it is also possible to use saturated, unsaturated or aromatic cyclic dicarboxylic anhydrides of the formulae (V) and (VI) as comonomers in addition to the epoxy group-bearing alkoxysilanes of the formula (I) useable in accordance with the invention and optionally further epoxides of the formula (II) and (III) under the conditions of the DMC-catalysed alkoxylation

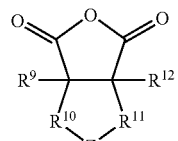

(V)

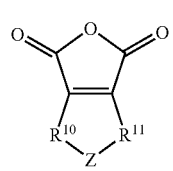

(VI)

where $R^9$, $R^{10}$, $R^{11}$ and $R^{12}$ are each independently hydrogen or alkyl, alkenyl, alkoxy, aryl or aralkyl groups. The hydrocarbon radical may be bridged cycloaliphatically or aromatically via the fragment Z, where Z may be either a divalent alkylene radical or alkenyl radical. Cyclic anhydrides used with preference are succinic anhydride, oct(en)yl-, dec(en)yl- and do-dec(en)ylsuccinic anhydride, maleic anhydride, phthalic anhydride, hexahydro-, tetrahydro-, dihydro-, methylhexahydro- and methyltetrahydrophthalic anhydride. During the alkoxylation process, the particular anhydride monomers can be copolymerized in any sequence and in a variable amount successively or simultaneously in parallel to the epoxide feed with ring opening to give polyetheresters. It is also possible to use mixtures of anhydrides of the formula (V) and (VI).

When the alkoxylation of epoxy-functional alkoxysilanes—optionally in the presence of further epoxide compounds of the (II) or (III) type or comonomers according to (V) and (VI)—is carried out in the presence of carbon dioxide, it is possible to prepare carbonate group-modified polyethers or polyetheresters through insertion of carbon dioxide into the modified polymer chain. Such reactions take place preferably in autoclave reactors under elevated pressure and a carbon dioxide atmosphere. The carbonate content is variable and is controllable, for example, through the selection of the temperature and pressure conditions during the reaction.

The starters or starter compounds used for the alkoxylation reaction may be all compounds of the formula (VII)

$$R^1-H \quad (VII)$$

(the H belongs to the OH group of an alcohol or of a phenolic compound) alone or in mixtures with one another which, according to formula (VII), have at least one reactive hydroxyl group. $R^1$ corresponds to a saturated or unsaturated, optionally branched radical, or is a polyether radical of the alkoxy, arylalkoxy or alkylarylalkoxy group type, in which the carbon chain may be interrupted by oxygen atoms, or $R^1$ is a singularly or multiply fused aromatic group to which a phenolic OH group is bonded directly. The chain length of the polyether radicals which have alkoxy, arylalkoxy or alkylarylalkoxy groups and are useable as the starter compound is adjustable at will. The polyether, alkoxy, arylalkoxy or alkylarylalkoxy group preferably contains 1 to 1500 carbon atoms, more preferably 2 to 300 carbon atoms, especially 2 to 100 carbon atoms.

In the context of the present invention, starter compounds are understood to mean substances which form the start of the polyether molecule to be prepared, which is obtained by the inventive addition of epoxy-functional monomers of the formulae (I), (II) and (III) and possibly further comonomers of the formulae (IV), (V) and (VI). The starter compound used in the process according to the invention is preferably selected from the group of the alcohols, polyetherols or phenols. Preference is given to using, as the starter compound, a mono- or polyhydric polyether alcohol or alcohol $R^1$—H (the H belongs to the OH group of the alcohol or phenol).

The OH-functional starter compounds $R^1$—H (VII) used are preferably compounds having molar masses of 18 to 10 000 g/mol, especially 50 to 2000 g/mol, and having 1 to 8, preferably having 1 to 4, hydroxyl groups.

Examples of compounds of the formula (VII) include allyl alcohol, butanol, octanol, dodecanol, stearyl alcohol, 2-ethylhexanol, cyclohexanol, benzyl alcohol, ethylene glycol, propylene glycol, di-, tri- and polyethylene glycol, 1,2-propylene glycol, di- and/or polypropylene glycol, poly-THF, OH-functional poly olefins, OH-functional poly-butadien, 1,4-butanediol, 1,6-hexanediol, 1,4-butindiol (triple CC-bond), tetramethyl decindiol, trimethylolpropane, glycerol, pentaerythritol, sorbitol, cellulose sugar, lignin or also further compounds which are based on natural substances and bear hydroxyl groups.

Advantageously, low molecular weight polyetherols having 1-8 hydroxyl groups and molar masses of 50 to 2000 g/mol, which have in turn been prepared beforehand by DMC-catalysed alkoxylation, are used as starter compounds.

In addition to compounds with aliphatic and cycloaliphatic OH groups, any compounds having 1-20 phenolic OH functions are suitable. These include, for example, phenol, alkyl and arylphenols, bisphenol A and novolacs.

To start the alkoxylation reaction, in the process according to the invention, the starter mixture consisting of one or more OH-functional starter compounds of the formula (VII) and the double metal cyanide catalyst, which has optionally been slurried beforehand in a suspension medium, are initially charged in the reactor. The suspension media used may either be a polyether or inert solvents, or advantageously also one or more starter compounds of the formula (VII), or alternatively a mixture of the two components. At least one of the epoxide compounds of the formula (I), (II) or (III) is metered into the initially charged starter mixture. To start the alkoxylation reaction and to activate the double metal cyanide catalyst, usually at first at least only a portion of the total amount of epoxide to be metered in is added. The molar ratio of epoxide to the reactive groups of the starter, especially the OH groups in the starter mixture, in the start phase is preferably 0.1 to 10:1, preferably 0.2 to 5:1, especially 0.4 to 3:1. It may be advantageous when the addition of the epoxide is preceded by removal of any reaction-inhibiting substances present from the reaction mixture, for example by distillation.

The start of the exothermic reaction can be detected, for example, by monitoring the pressure and/or temperature. A sudden decline in the pressure in the reactor indicates in the case of gaseous alkylene oxides that the alkylene oxide is being incorporated, the reaction has thus started and the end of the start phase has been attained. In the case of nongaseous glycidyl ethers/esters or epoxy-functional alkoxysilanes, the startup of the reaction is indicated by the onset of exothermicity.

After the start phase, i.e. after initiation of the reaction, according to the desired molar mass, either simultaneously further starter compound and further epoxide or only further epoxide are metered in. Alternatively, it is also possible to add on any mixture of different epoxides of the formulae (I), (II) and (III). The epoxide monomers of the formulae (I), (II) and (III) useable in accordance with the invention can also be added on in succession in any sequence. The reaction can, for example, be carried out in an inert solvent for the purpose of lowering the viscosity of the reaction mixture. Suitable inert solvents are hydrocarbons, especially toluene, xylene or cyclohexane.

In the inventive products, the molar ratio of the sum of the epoxides metered in, including the epoxides already added in the start phase, based on the starter compound used, more particularly based on the number of OH groups of the starter compound used, is preferably 1 to $10^5$:1, especially 1 to $10^4$:1.

The epoxide compounds are added on preferably at a temperature of 60 to 250° C., more preferably at a temperature of 90 to 160° C. The pressure at which the alkoxylation takes place is preferably 0.02 bar to 100 bar, more preferably 0.05 to 20 bar and especially 0.2 to 2 bar absolute. The performance of the alkoxylation under reduced pressure allows the reaction to be performed very safely. Optionally, the alkoxylation can be performed in the presence of an inert gas (e.g. nitrogen) or—to prepare polyether carbonates—in the presence of carbon dioxide, also at a reduced pressure which is then preferably 1 to 20 bar absolute.

The lactones (IV) or cyclic anhydrides (V) and (VI) useable for the preparation of ester-modified polyethers can either be added to the starter-catalyst mixture as early as in the start phase or added at a later time in parallel to the epoxide addition. The comonomers mentioned can also each be metered into the reactor in alternating succession with epoxides.

The molar ratio of the epoxide monomers to cyclic anhydrides is variable. Typically, at least equimolar amounts of epoxide monomers based on anhydrides are used. Preference is given to the use of the epoxides in a molar excess in order to ensure the full anhydride conversion.

Lactones can be added during the alkoxylation either in a stoichiometric deficiency or excess based on the epoxide monomers.

For the preparation of carbonate-modified polyethers, the alkoxylation takes place in the presence of either gaseous carbon dioxide or of solid carbon dioxide supplied in the form of dry ice. Preference is given to using carbon dioxide gas, which can be supplied either before the start of the reaction, i.e. actually during the initialization stage, to the system composed of starter and DMC catalyst, or during the subsequent phase of feeding of epoxide monomers and possibly further comonomers. In order to increase the carbonate content in the end product, it is advantageous, according to the carbon dioxide combustion, recognizable by the pressure decrease in the autoclave, in the course of the reaction, to meter in further carbon dioxide continuously or in portions. The reaction is preferably effected at pressures of less than 100 bar, more preferably at less than 20 bar.

After the monomer addition and any postreaction to complete the monomer conversion, any residues of unreacted monomer and any further volatile constituents present are removed, typically by vacuum distillation, gas stripping or other methods of deodorization. Volatile secondary components can be removed either batchwise or continuously. In the process according to the invention based on DMC catalysis, a filtration can normally be dispensed with.

The process steps can be performed at identical or different temperatures. The mixture of starter substance, DMC catalyst and optionally suspension medium initially charged in the reactor at the start of the reaction can be pretreated by stripping before the start of monomer addition according to the teaching of Wo 98/52689. In this case, an inert gas is mixed into the reaction mixture via the reactor feed and volatile components are removed from the reaction mixture by applying a reduced pressure with the aid of a vacuum system connected to the reactor system. In this simple manner, substances which can inhibit the catalyst, for example lower alcohols or water, can be removed from the reaction mixture. The addition of inert gas and the simultaneous removal of the volatile components may be advantageous especially in the startup of the reaction, since the addition of the reactants or side reactions can also allow inhibiting compounds to get into the reaction mixture.

The DMC catalysts used may be all known DMC catalysts, preferably those which comprise zinc and cobalt, preferentially those which comprise zinc hexacyanocobaltate(III). Preference is given to using the DMC catalysts described in U.S. Pat. No. 5,158,922, US 20030119663, WO 01/80994 or in the documents cited above. The catalysts may be amorphous or crystalline. In the reaction mixture, the catalyst concentration is preferably >0 to 1000 ppmw (ppm by mass), preferentially >0 to 500 ppmw, more preferably 0.1 to 200 ppmw and most preferably 1 to 50 ppmw. This concentration is based on the total mass of the polyetherpolyols formed.

Preference is given to metering the catalyst into the reactor only once. The amount of catalyst should be adjusted so as to give a sufficient catalytic activity for the process. The catalyst can be metered in as a solid or in the form of a catalyst suspension. When a suspension is used, the starter of the formula (VII) in particular is suitable as a suspension medium. However, preference is given to dispensing with suspension.

The process according to the invention provides polyethers which are notable in that they, with regard to structure and molar mass, can be prepared in a controlled manner and reproducibly. The sequence of the monomer units can be varied within wide limits. Epoxide monomers of the (I), (II) and (III) type and lactones of the formula (IV) may be in any blockwise sequence or be incorporated randomly into the modified polymer chain. The fragments inserted into the forming modified polymer chain by the reaction with ring opening of the reaction components of the formulae (I) to (VI) are freely permutable with one another in their sequence, with the restriction that cyclic anhydrides of the formula (V) and (VI) and carbon dioxide are present inserted randomly, i.e. not in homologous blocks, in the polyether structure.

When p in formula (I) is greater than 1, the process according to the invention forms highly functionalized networks in which polyether chains which are each started by $R^1$ and which contain the fragments freely permutable in their sequence, which have been inserted by the reaction with ring opening of the reaction components of the formulae (I) to (VI) into the forming modified polymer chain, are bonded to one another via $—CH_2—O—(CH_2)_{2+c}—Si—(CH_2)_{2+c}—O—CH_2—$ bridges. They thus form highly complex, highly functionalized structures. Here too, it is possible to adjust the functionalities to a desired field of use in a controlled manner. The alkoxylation of mixtures of mono-, di- or tri-epoxy-functional alkoxysilane compounds of the formula (I) allows p, on average, to assume any values between 1 and 3. The degree of crosslinking and the complexity of the resulting modified polymer structures rises with increasing mean value of p. Preference is given to p mean epoxy functionality between 1 and 2 determined by the index p. Very particular preference is given to 3-glycidyloxyalkyltrialkoxysilanes where p is 1.

The fragments which have been inserted into the forming modified polymer chain by the reaction with ring opening of the reaction components of the formulae (I) to (VI), in block form or in random distribution in the context of the above definitions, may occur not only in the chain of a polyether structural unit but also distributed randomly over the multitude of the polyether structural units which have been formed and are bonded to one another via $—CH_2—O—(CH_2)_{2+c}—Si—(CH_2)_{2+c}—O—CH_2—$ bridges. The manifold nature of the structural variations of the process products does not permit any clear description in terms of formula. Preference is given to preparing the inventive polyether structures of the formula (VIII)—see FIG. 1—where mono-epoxy-functional alkoxysilanes of the formula (I) with the indices p equal to 1 and a equal to 3 are alkoxylated. These consist of linear chains which are substituted by trialkoxysilyl groups and are highly functionalized in a controlled manner by virtue of the selection of the fragments d to j, according to the fragments inserted into the modified polymer chain by the reaction with ring opening of the reaction components of the formulae (I) to (VI) and hence can be tailored for different fields of application.

The substituents R, $R^1$-$R^2$, the Y and Z radicals and the indices a, b and c correspond to the definitions given above for the compounds of the formulae (I) to (VII), where d is an integer of 1 to 1000, preferably 1 to 100, more preferably 4 to 20 and especially 5 to 10, and especially greater than 4, e is an integer of 0 to 10 000, preferably 1 to 2000, more preferably 1 to 1000 and especially 1 to 500, f is an integer of 0 to 1000, preferably 0 to 100, more preferably 0 to 50 and especially 0 to 30, g is an integer of 0 to 1000, preferably 0 to 200, more preferably 0 to 100 and especially 0 to 70, h, i and j are integers of 0 to 500, preferably 0 to 300, more preferably 0 to 200 and especially 0 to 100, and with the proviso that the fragments with the indices d to j are freely permutable with one another, i.e. are exchangeable for one another in the sequence within the polyether chain, n is an integer from 2 to 8;

and preferably, furthermore, p is 1 and a is 3.

The different monomer units, both of the fragments with the indices d to j and of any polyoxyalkylene chain of the substituent $R^1$ present, may be in an alternating blockwise structure or else be subject to a random distribution.

The indices and the value ranges of the indices specified which are reproduced in the formulae cited here should therefore be understood as mean values of the possible random distribution of the structures actually present and/or mixtures thereof. This is also true of structural formulae reproduced exactly in principle as such, for example for formula (VIII).

It is possible by the process according to the invention, according to the epoxy-functional alkoxysilane of the formula (I) used and any further monomers corresponding to the formulae (II), (III), (IV), (V) and (VI) used, and possibly also carbon dioxide, in the process according to the invention, likewise to prepare inventive alkoxysilyl group-modified polyether alcohols, and any mixtures thereof.

Individual known representatives of the compounds of the formula (VIII) with exclusively terminal trialkoxysilyl groups have been described in Japanese Patent Application JP 2005-215422 and in European Patent Application EP-A1-0-101027, and also in "Polymer (Korea)", (2003), Vol. 27(3), pages 265-270 (Title of the article: Properties of polymer electrolytes based on polyethylene oxide/lithium perchlorate ($PEO$-$LiClO_4$) matrix fabricated by sol-gel process), but in all citations by different processes, i.e. not by alkoxylation of epoxides of the formula (I) and also exclusively limited to polyether chains formed from the monomers ethylene oxide or propylene oxide and with terminal single trialkoxysilyl functionalization.

The compounds described there are:

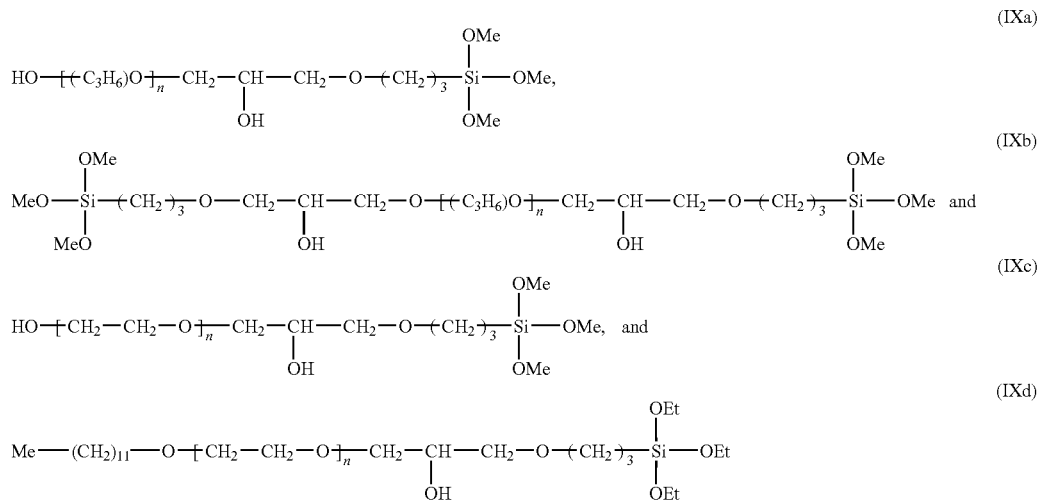

This invention thus further provides novel compounds prepared by the process according to the invention, with the proviso that the compounds (IXa), (IXb) and (IXc) and (IXd) are not included. Preference is given to the compounds of the formula (VIII), with the proviso that the compounds (IXa), (IXb) and (IXc) and (IXd) are not included.

The invention further provides compounds prepared by the process according to the invention, in which $R^1$ is a polyether fragment and in which at least one fragment which has been inserted into the forming polymer chain by the reaction with ring opening of the reaction components of the formulae (I) to (VI) is present, with the proviso that the fragment formed in the ring opening of the compounds of the formula (I) is not terminal.

Preference is given to compounds of the formula (VIII) in which $R^1$ is a polyether fragment and in which at least one of the indices e to j is greater than or equal to 1, with the proviso that the fragment with the index d is not terminal.

$^{29}$Si—NMR— und GPC analysis show that transesterification reaction at the silicone atom may happen while the DMC catalysed reaction and/or while any later process step because of the presence of chain terminating OH-groups which are caused by the inventive process. Formally one of the alkyl groups bound to oxygen at the silicone atom will be exchanged by the long-chain modified alkoxysilyl polymer radical. Bimodal but also multi modal GPC curves proof the presence of alkoxylation products according to the invention forming the non-transesterificated species, as depicted in formula (VIII) together with those species having double, partial triple and even also fourfold molar mass. Formula (VIII) show the complexity of the chemical reality only in a simplified way.

A further object of the present invention are therefore compositions of compounds wherein the statistical average sum of the indices (a) plus (b) in formula (VIII) is less than 3, because a partial exchange of the OR-group by silylpolyether groups.

The composition contains species having a further molecule of formula (VIII) bound to the silicone atom, formed by condensation reaction of the reactive OH-group under elimination of R—OH. The reaction may take place several times until e.g. all RO-groups at the silicone atom have been exchanged by further molecules of formula (VIII).

The presence of more than one signal in typical $^{29}$Si—NMR spectra confirms the existence of silyl groups having a different substitution pattern.

The ranges and preferred ranges given in the present invention for the indices (a) to (j) shall therefore be read as average values over different, not being isolable species.

The invention further provides compounds prepared by the process according to the invention which do not contain any mono-alkoxysilyl-terminal species. Preference is given to compounds of the formula (VIII) which do not contain any mono-alkoxysilyl-terminal species.

The invention further provides all compounds prepared by the process according to the invention, excluding mono-alkoxysilyl-terminated species which form using exclusively those alkylene oxide monomers of the formula (II) in which, simultaneously, the $R^2$, $R^3$, $R^5$, $R^6$ radicals are either all hydrogen, or in which $R^2$, $R^3$, $R^5$ are each hydrogen and $R^6$ is methyl, or in which $R^2$, $R^3$, $R^6$ are each hydrogen and $R^5$ is methyl. Preference is given to all compounds of the formula (VIII), excluding those mono-alkoxysilyl-terminated species in which the index e is not 0 and which consist only of those alkylene oxide monomers of the formula (II) in which, simultaneously, the $R^2$, $R^3$, $R^5$, $R^6$ radicals are either all hydrogen, or in which $R^2$, $R^3$, $R^5$ are each hydrogen and $R^6$ is methyl, or in which $R^2$, $R^3$, $R^6$ are each hydrogen and $R^5$ is methyl.

The invention further provides compounds prepared by the process according to the invention in which at least one fragment formed by the reaction with ring-opening of the reaction components of the formulae (III) to (VI) has been inserted into the forming modified polymer chain. Preference is given to compounds of the formula (VIII) in which at least one of the indicies f, g, h, i and/or j is not 0.

The invention further provides compounds prepared by the process according to the invention in which $R^1$ of the starter compound is not a polyether fragment. Preference is given to compounds of the formula (VIII) in which $R^1$ is not a polyether fragment.

These novel, inventive reactive polyethers constitute curable modified polymers owing to their hydrolysis-sensitive alkoxysilyl groups which tend to crosslink. The crosslinking to give solid thermoset end products is effected in a simple manner in the presence of water and optionally with addition of acid or base as an accelerant. Increasing the temperature during the curing operation allows the pot life to be controlled. The process according to the invention permits the polymer structure of the inventive crosslinkable products to be varied in manifold ways according to the type of starter and the type, amount and sequence of epoxide monomers useable, and thus product properties important in application terms can be tailored as a function of the end use. For example, a variation in the proportion of alkoxysilane units in the modified polymer chain allows influence on the crosslinking density and hence the mechanical and physicochemical property profile of the cured modified polymers within wide limits. The incorporation of further comonomers such lactones, cyclic anhydrides, carbon dioxide or oxetanes opens up even further structural and property variations with formation of ester or carbonate groups in the modified polymer chain.

The modified polymers obtained by the process according to the invention are suitable, for example, as base materials for the production of adhesives and sealants, for surface coating, as reactive crosslinkers, as adhesion promoters and primers for various substrates, such as metals, glass and glass fibres/glass fabric, generally silicatic materials or else for surface treatment of, for example, pigments and fillers in coatings or plastics.

The process according to the invention for direct alkoxylation of alkoxysilanes bearing epoxy groups by means of DMC catalysis differs fundamentally from the procedures described so far in Patents DE 69831518 T2, JP 11021463, JP 08295805, JP 09012863, JP 09012861, JP 07062222. The inventive crosslinkable polyethers containing alkoxysilyl groups also differ significantly from the polyethers with exclusively terminal alkoxysilyl units described in Patents cited above. The means of direct alkoxylation of hydrolysis-sensitive, crosslinkable epoxy-functional alkoxysilanes, for example 3-glycidyloxypropyltrimethoxysilane and 3-glycidyloxypropyltriethoxysilane, provided by the novel process makes available an instrument which allows the advantages of DMC technology to be utilized further and a new class of crosslinkable modified polymers to be prepared. By means of the selection of the starter compound having reactive hydrogen, the type of epoxy-functional alkoxysilanes used, which may be used in combination with alkylene oxides or other glycidyl compounds, and by virtue of the variation of the composition of mixtures of these epoxide compounds and the sequence of their addition during the DMC-catalysed alkoxylation process, the modified polymer structure and their properties can be adjusted virtually as desired.

The reactors used for the reaction claimed in accordance with the invention may in principle be all suitable reactor types which can control the reaction and any exothermicity which may be present.

The reaction can be effected, in a manner known in process technology terms, continuously, semicontinuously or else batchwise, and can be matched flexibly to the production equipment available.

In addition to conventional stirred tank reactors, it is also possible to use jet loop reactors with a gas phase and internal heat exchanger tubes, as described in WO 01/062826. It is additionally possible to use gas phase-free loop reactors.

In the metered addition of the reactants, good distribution of the substances involved in the chemical reaction, i.e. of the epoxide monomers, starters, DMC catalyst and if appropriate suspension media or comonomers such as lactones, anhydrides or carbon dioxide, is necessary.

The inventive polyethers and the corresponding processes for their preparation are described below by way of example, without the invention being considered to be restricted to these illustrated embodiments.

Where ranges, general formulae or compound classes are specified below, these shall encompass not just the corresponding ranges or groups of compounds which are mentioned explicitly but also all sub-ranges and sub-groups of compounds which can be obtained by selecting individual values (ranges) or compounds.

WORKING EXAMPLES

In the examples adduced below, the present invention is described by way of example, without the invention, whose scope of application is evident from the entire description and the claims, being interpreted as restricted to the embodiments cited in the examples.

Preparation of Polyether Alcohols Bearing Alkoxysilyl groups by the process according to the invention with the aid of DMC catalysts. OH numbers were determined by the cold acetylation method based on the analysis method C-V 17A (98) of the Deutsche Gesellschaft für Fettwissenschaft (DGF); (German Society for Fat Science). The mean molar masses were determined by calculation from the OH numbers thus determined. The epoxide oxygen content of the end products was determined in the presence of conc. HCl by the principle of back-titration with sodium hydroxide solution.

Example 1

A 3 litre autoclave is initially charged with 130.2 g of polypropylene glycol monobutyl ether (mean molar mass 520 g/mol) and 0.10 g of zinc hexacyanocobaltate DMC catalyst under nitrogen and heated to 130° C. with stirring. The reactor is evacuated down to an internal pressure of 30 mbar in order to remove any volatile constituents present by distillation. To activate the DMC catalyst, a portion of 58.0 g of propylene oxide is fed in. After 15 min and startup of the reaction (decline in internal reactor pressure), simultaneously and from two different reservoir vessels, 556.0 g of 3-glycidyloxypropyltriethoxysilane (DYNASYLAN® GLYEO) and 1363.0 g of propylene oxide are metered in continuously and with cooling at 130° C. and max. internal reactor pressure 0.9 bar absolute within 30 min. The 90-minute postreaction at 130-150° C. is followed by the degassing stage. In this stage, volatile fractions such as residual propylene oxide are distilled off under reduced pressure. The finished low-viscosity and colourless polyether is cooled to below 80° C. and discharged from the reactor.

The resulting polyetherol contains an average per molecule of 8 trialkoxysilyl units, has an OH number of 7.6 mg KOH/g and a mean molar mass of 7400 g/mol. Free epoxide groups are undetectable in the end product.

Example 2

A 3 litre autoclave is initially charged with 200.0 g of polypropylene glycol monobutyl ether (mean molar mass 750 g/mol) and 0.015 g of zinc hexacyanocobaltate DMC catalyst under nitrogen. The mixture is heated to 130° C., then freed of any volatile constituents at 30 mbar. To activate the DMC catalyst, a portion of 225.0 g of 3-glycidyloxypropyltriethoxysilane (DYNASYLAN® GLYEO) is fed in. After the reaction has started up (slight exothermicity) and DYNASYLAN® GLYEO has been depleted, first 59.1 g of ethylene oxide within 10 min and finally a further 225.0 g of 3-glycidyloxypropyltriethoxysilane (DYNASYLAN® GLYEO) within 20 min are metered in with cooling at 130° C. and max. internal reactor pressure 0.8 bar absolute. The 90-minute postreaction at 130-150° C. is followed by the degassing stage in order to remove volatile fractions.

The resulting polyetherol is formed from DYNASYLAN® GLYEO and ethylene oxide blocks, is of low viscosity, contains an average per molecule of 6 trialkoxysilyl units, and has an OH number of 22.4 mg KOH/g and a mean molar mass of 2500 g/mol. Free epoxy groups are undetectable in the end product.

Example 3

A 3 litre autoclave is initially charged with 65.1 g of 1-octanol and 0.065 g of zinc hexacyanocobaltate DMC catalyst under nitrogen. The mixture is heated to 130° C. and then freed of any volatile constituents at 400 mbar. To activate the DMC catalyst, a portion of 58.0 g of propylene oxide is fed in. After the reaction has started up (decline in internal pressure), successively each at 130° C., first 236.0 g of 3-glycidyloxypropyltrimethoxysilane (DYNASYLAN® GLYMO) within 35 min, then, after a postreaction time of 30 min, 220.0 g of ethylene oxide within 10 min with cooling and max. internal reactor pressure 1.5 bar absolute are metered in. The 90-minute postreaction at 150° C. is followed by the degassing stage in order to remove volatile fractions.

The resulting polyetherol is formed from a DYNASYLAN® GLYMO and ethylene oxide block, contains an average per molecule of 2 trialkoxysilyl units, and has an OH number of 49.4 mg KOH/g and a mean molar mass of 1160 g/mol. Free epoxy groups are undetectable in the end product.

Example 4

A 3 litre autoclave is initially charged with 200.0 g of polypropylene glycol monoallyl ether (mean molar mass 520 g/mol) and 0.017 g of zinc hexacyanocobaltate DMC catalyst under nitrogen. The mixture is heated to 130° C. and freed of any volatile constituents at 30 mbar. To activate the DMC catalyst, a portion of 50.0 g of propylene oxide is fed in. After the reaction has started up (decline in internal pressure), 319.0 g of 3-glycidyloxypropyltrimethoxysilane (DYNASYLAN® GLYMO) are added at 125° C. within 40 min. A postreaction time of 120 min at 130-140° C. is followed by the degassing stage, in order to remove volatile fractions. The resulting low-viscosity, colourless polyetherol contains a terminal DYNASYLAN® GLYMO block (average per molecule of 5 trialkoxysilyl units), and has an OH number of 27.5 mg KOH/g and a mean molar mass of 2040 g/mol. Free epoxy groups are undetectable in the end product.

Example 5

A 3 litre autoclave is initially charged with 375.0 g of polypropylene glycol monobutyl ether (mean molar mass 750 g/mol) and 0.250 g of zinc hexacyanocobaltate DMC catalyst under nitrogen. The mixture is heated to 130° C. and then freed of any volatile constituents at 30 mbar. To activate the DMC catalyst, a portion of 58.0 g of propylene oxide is fed in. After startup of the reaction (decline in internal pressure), 588.0 g of a homogeneous mixture of 3-glycidyloxypropyltriethoxysilane (DYNASYLAN® GLYEO, 417.0 g) and ε-caprolactone (171.0 g) are added at 130-150° C. within 60 min. After a postreaction time of 120 min at 120-130° C., 725.0 g of propylene oxide are added continuously at 130° C. and an internal reactor pressure of max. 1 bar absolute within 15 min. Another postreaction of 30 min at 130° C. is followed by the degassing stage in order to remove volatile fractions. The resulting pale yellowish polyetherester contains a block of randomly distributed trialkoxysilyl and ester units (average of 3 mol each of DYNASYLAN® GLYEO and ε-caprolactone per polymer molecule), followed by a terminal 25 mol propylene oxide block, and has an OH number of 17.0 mg KOH/g and a mean molar mass of 3300 g/mol. Free epoxy groups are undetectable in the end product.

Example 6

A 3 litre autoclave is initially charged with 375.0 g of polypropylene glycol monobutyl ether (mean molar mass 750 g/mol) and 0.16 g of zinc hexacyanocobaltate DMC catalyst under nitrogen. The mixture is heated to 130° C. and then freed of any volatile constituents at 30 mbar. To activate the DMC catalyst, a portion of 354.3 g of 3-glycidyloxypropyltrimethoxysilane (DYNASYLAN® GLYMO) is fed in. After the reaction has started up and DYNASYLAN® GLYMO has been depleted, the mixture is cooled to 110° C. Gaseous carbon dioxide is metered in to the autoclave up to an internal pressure of 5 bar absolute. 1740.0 g of propylene oxide are added continuously at 110° C. with cooling within 110 min. A decline in pressure to below 5 bar signals the depletion of carbon dioxide. During the propylene oxide addition, further carbon dioxide is metered in in portions in order to keep the internal reactor pressure between 4 and 5 bar. After 90 min of postreaction at 110° C. and a decline in pressure to <2 bar, the mixture is degassed under reduced pressure in order to remove volatile fractions.

The resulting low-viscosity polyethercarbonate contains a DYNASYLAN® GLYMO block (average per molecule of 3 trialkoxysilyl units) and a 60 mol propylene oxide block, in which the carbonate groups are in random distribution. The product has an OH number of 12 mg KOH/g and a mean molar mass of 4675 g/mol. The carbonate content is approx. 4% by weight. Free epoxy groups are undetectable in the end product.

Example 7

A 3 litre autoclave is initially charged with 375.0 g of polypropylene glycol monobutyl ether (mean molar mass 750 g/mol), 154.0 g of hexahydrophthalic anhydride (HHPSA) and 0.350 g of zinc hexacyanocobaltate DMC catalyst under nitrogen. The mixture is heated to 130° C. and then freed of any volatile constituents at 30 mbar. To activate the DMC catalyst, a portion of 58.0 g of propylene oxide is fed in. After the reaction has started up (decline in internal pressure), 418.0 g of 3-glycidyloxypropyltriethoxysilane (DYNASYLAN® GLYEO) are added at 130° C. within 20 min. After a postreaction time of 150 min at 130-150° C., the reaction mixture is cooled to 130° C. Addition of 435.0 g of propylene oxide at 130° C. within 15 min is followed by the degassing stage, in order to remove volatile fractions.

The resulting colourless polyetherester contains an average per molecule of 2 mol of HHPSA and 3 mol of DYNASYLAN® GLYEO in a randomly mixed sequence, followed by a 30 mol end block of propylene oxide units. The OH number is 23.0 mg KOH/g, the mean molar mass 2440 g/mol. Free epoxy groups are undetectable in the end product.

Example 8

A 3 litre autoclave is initially charged with 214.0 g of polypropylene glycol monoallyl ether (mean molar mass 430 g/mol), 278.2 g of 3-glycidyloxypropyl-triethoxysilane (DYNASYLAN® GLYEO) and 0.225 g of zinc hexacyanocobaltate DMC catalyst under nitrogen. The mixture is heated to 150° C., then freed of any volatile constituents at 30 mbar. After a hold time of 30 min at 150° C. and activation of the DMC catalyst, the reaction mixture is cooled to 130° C. Thereafter, 348.0 g of propylene oxide are fed in at max. internal pressure 1 bar within 15 min. In each case at 130° C. and max. internal pressure 1 bar absolute, 114.0 g of ε-caprolactone within 25 min, 216.1 g of 1,2-butylene oxide within 15 min, 236.2 g of 3-glycidyl-oxypropyltrimethoxysilane (DYNASYLAN® GLYMO) within 45 min, 120.0 g of styrene oxide within 15 min and finally 290 g of propylene oxide within 40 min are added successively. The addition of each portion is followed by an about 15-minute hold time at 130° C. before the next monomer is metered in. The metered addition of the propylene oxide end block is followed by a postreaction time of 30 min at 130° C. Finally, degassing is effected, in order to remove volatile fractions.

The resulting pale yellowish aromatically modified polyetherester contains an average per molecule, in successive blocks, 2 mol of DYNASYLAN® GLYEO, 12 mol of propylene oxide, 2 mol of ε-caprolactone, 6 mol of 1,2-butylene oxide, 2 mol of DYNASYLAN® GLYMO, 2 mol of styrene oxide and 10 mol of propylene oxide as an end block. The OH number is 18.0 mg KOH/g, the mean molar mass 3120 g/mol. Free epoxy groups are undetectable in the end product.

Having thus described in detail various embodiments of the present invention, it is to be understood that the invention defined by the above paragraphs is not to be limited to particular details set forth in the above description as many apparent variations thereof are possible without departing from the spirit or scope of the present invention.

The invention claimed is:

1. A process for preparing polyether alcohols having alkoxysilyl groups by means of DMC catalysis, characterized in that one or more epoxy-functional alkoxysilanes are added individually or in a mixture with further epoxide compounds and optionally further comonomers, either in block form or in random distribution, onto a chain starter of the formula (VII)

$$R^1\text{—H} \quad (VII)$$

having at least one reactive hydroxyl group, where $R^1$ is a saturated or unsaturated, optionally branched radical, or a polyether radical of the alkoxy, arylalkoxy or alkylarylalkoxy group type, in which the carbon chain may be interrupted by oxygen atoms or corresponds to a polyetheralkoxy radical or to a singularly or multiply fused phenolic group.

2. The process according to claim 1, characterized in that the epoxy-functional alkoxysilane used is a compound of the formula (I)

$$\left[\overset{O}{\triangle}\diagup\diagdown_O\diagup\right]_p \text{Si} R^b_{...} (O{-}R)_a \quad (I)$$

where

R corresponds to one or more identical or different radicals selected from linear and branched, saturated, monounsaturated and polyunsaturated alkyl radicals having 1 to 20 carbon atoms and haloalkyl groups having 1 to 20 carbon atoms, and a is an integer of 1 to 3, b is an integer of 0 to 2, and the sum of a and b is equal to 3, c is an integer of 0 to 24 and p is an integer which is the difference of 4-a-b.

3. The process according to claim 1, characterized in that the reaction is carried out in solvents or suspension media and/or mixtures thereof.

4. The process according to claim 1, wherein one or more epoxy-functional alkoxysilanes of the formula (I)

$$\left[\overset{O}{\triangle}\diagup\diagdown_O\diagup\right]_p \text{Si} R^b (O{-}R)_a \quad (I)$$

are added individually or in a mixture with further epoxide compounds of the formulae (ii)

(II) — structure with $R^3$, $R^5$, $R^2$, $R^6$, Y, O and/or (III)

(III) — structure with $R^2$, epoxide, $O{-}R^4$ and/or optionally further comonomers such as lactones (IV), (IV) — lactone structure with $[R^7]_n$, C, $R^8$, O and/or cyclic anhydrides (V), (VI), (V) — anhydride structure with $R^9$, $R^{10}$, $R^{11}$, $R^{12}$, Z -continued

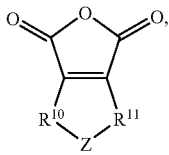

(VI)

and/or carbon dioxide and/or oxetanes, either in block form or in random distribution, onto the chain starter of the formula (VII)

where

R corresponds to one or more identical or different radicals selected from linear and branched, saturated, monounsaturated and polyunsaturated alkyl radicals having 1 to 20 carbon atoms and haloalkyl groups having 1 to 20 carbon atoms, and $R^2$ and $R^3$, and $R^5$ and $R^6$, are the same or else are each independently H or a saturated or optionally mono- or polyunsaturated, optionally mono- or polyvalent hydrocarbon radical which also has further substitution, where the $R^5$ and $R^6$ radicals are a monovalent hydrocarbon radical, and the hydrocarbon radical may be bridged cycloaliphatically via the fragment Y, where Y may be absent or else is a methylene bridge having 1 or 2 methylene units, with the proviso that, when Y is absent, the $R^2$ or $R^3$ radicals are each independently a linear or branched radical having 1 to 20 carbon atoms, $R^4$ is a glycidyloxypropyl group which is bonded via an ether or ester function to a linear or branched alkyl radial of 1 to 24 carbon atoms or via an aromatic or cycloaliphatic radical, n is an integer of 2 to 8 and $R^7$ and $R^8$ are each independently hydrogen or alkyl, alkoxy, aryl or aralkyl groups, and $R^9$, $R^{10}$, $R^{11}$ and $R^{12}$ are each independently hydrogen or alkyl, alkenyl, alkoxy, aryl or aralkyl groups, where the alkyl radical or alkenyl radical may be bridged cycloaliphatically or aromatically via the Z fragment, where Z may be either a divalent alkylene radical or alkenylene radical.

5. The process according to claim 4, characterized in that the epoxide components, lactones, cyclic anhydrides of the formulae (I) to (VI) are metered in alone or in mixtures with one another in any sequence and in variable amounts successively or simultaneously in parallel to one another or else each in successive alternation.

6. The process according to claim 4, characterized in that the alkoxylation of the epoxy-functional alkoxysilanes (I), optionally in the presence of further epoxide compounds of the formula (II) or (III) and/or comonomers of the formula (IV), (V) and/or (VI), is carried out in the presence of carbon dioxide.

7. The process according to claim 6, characterized in that carbonate group-modified polyethers or polyetheresters are prepared by insertion of carbon dioxide into the modified polymer chain.

8. The process according to claim 1, characterized in that the starters of the formula $R^1$—H (VII) used are compounds having molar masses of 18 to 10 000 g/mol and having 1 to 8 hydroxyl groups in the molecule and/or low molecular weight polyetherols having 1-8 hydroxyl groups and molar masses of 50 to 2000 g/mol.

9. The process according to claim 1, characterized in that the starters of the formula $R^1$—H (VII) used are allyl alcohol, butanol, octanol, dodecanol, stearyl alcohol, 2-ethylhexanol, cyclohexanol, benzyl alcohol, ethylene glycol, propylene glycol, di-, tri- and polyethylene glycol, 1,2-propylene glycol, di- and/or propylene glycol, poly-THF, OH-functional poly olefins, OH-functional poly-butadien, 1,4-butanediol, 1,6-hexanediol, 1,4-butindiol, tetramethyl decindiol, trimethylol propane, glycerol, pentaerythritol, sorbitol, cellulose sugar, lignin or also and/or phenol, alkyl- and arylphenols, bisphenol A and novolacs.

10. The process according to claim 4, characterized in that the molar ratio of monomers and epoxy-functional compounds (I) to (VI) relative to reactive groups, in the products is 1 to $10^5$:1.

11. The process according to claim 10, characterized in that the reactive groups are —OH groups.

12. The process according to claim 1, characterized in that the reaction is effected continuously, semicontinuously or else batchwise.

* * * * *